United States Patent [19]

Krbechek

[11] Patent Number: 5,302,748
[45] Date of Patent: Apr. 12, 1994

[54] ESTERIFICATION PROCESS

[75] Inventor: Leroy O. Krbechek, Santa Rosa, Calif.

[73] Assignee: Henkel Corporation, Plymouth Meeting, Pa.

[21] Appl. No.: 16,377

[22] Filed: Feb. 11, 1993

[51] Int. Cl.$^5$ .............................................. C07C 69/52
[52] U.S. Cl. ..................................... 560/265; 560/205
[58] Field of Search ................................ 560/265, 205

[56] References Cited

U.S. PATENT DOCUMENTS 4,175,012 11/1979 Mackay et al. ..................... 204/108
5,151,547 9/1992 Sato et al. ....................... 560/265 X Primary Examiner—Arthur C. Prescott
Attorney, Agent, or Firm—Ernest G. Szoke; Wayne C. Jaeschke; Patrick J. Span

[57] ABSTRACT

An improved process for preparing esters of an alcohol and a carboxylic acid employing sulfuric acid in an amount effective to both catalyze the reaction and to remove or immobilize the water of reaction whereby an ester is provided in increased yield and purity. Esters of long chain acids are useful for the preparation of diketones which find utility as metal extractants.

22 Claims, No Drawings

ESTERIFICATION PROCESS

BACKGROUND OF THE INVENTION

1. Field of the Invention

This invention relates to an improved process for the preparation of esters of carboxylic acids and in particular to the preparation of lower alkyl (1 to 4 carbons) esters of carboxylic acids (8 to 22 carbons) which are useful in the preparation of beta diketones which are water insoluble and water immiscible and suitable for extraction of metal values.

2. Statement of Related Art

Esters of acids are important from the industrial standpoint as a great variety of commercial products are based on such esters. The classical method of preparing esters involves the reaction of an acid with an alcohol, usually in the presence of a catalyst to afford an ester and water.

$$RCOOH + R'OH \rightarrow RCOOR' + H_2O$$

The process is reversible and quantitative yields by simple reaction of the acid and alcohol are not obtained in the equilibrium reaction mixture. The catalyst's sole function is to hasten the attainment of equilibrium and does not affect the final composition at equilibrium. Generally, equilibrium is forced to the right in the equation by the removal of water as it is formed such as by application of mild vacuum to the reaction mixture. Alternative methods include the addition of other materials to form an azeotropic mixture with the water which azeotropic mixture is removed. Another attempt to effect high conversion requires the addition of large molar excesses of either the acid or alcohol, usually the least expensive material, or material with the lowest boiling point being used in excess in commercial practice.

Lower alkyl (1 to 4 carbon) esters of carboxylic acids have been employed in the past to prepare $\beta$-diketones which are useful in the extraction of metal values as described in commonly assigned U.S. Pat. No. 4,175,012. As described therein, the diketone is prepared by condensation of the ester with a compound containing an acetyl moiety in the presence of sodium hydride and an inert organic solvent. In the preparation of the ketone it is desirable that the ester be of a high purity.

DESCRIPTION OF THE INVENTION

In this description, except in the operating examples or where expressly indicated otherwise, all numbers describing amounts of ingredients or reaction conditions, are to be understood as modified by the word "about" in describing the broadest scope of the invention. Practice of the invention within the exact numerical limits is, however, generally preferred.

It has now been discovered that the use of a significant excess of sulfuric acid in the reaction provides unexpectedly high yields of the desired ester and the ester is of high purity. The sulfuric acid not only acts as a catalyst for the reaction but the excess acid further unites with, dessicates, removes or immobilizes the water of reaction by forming a second phase, resulting in an increased yield of the ester, in excess of 90% of the acid being converted to the ester. The ester further is of high purity of about 99%. While the present invention is applicable to any esterification of a carboxylic acid with an alcohol, it is of particular interest to the esterification of longer chain carboxylic acids such as the branched acids having about 6 to about 22 carbon atoms with lower alkyl alcohols containing from 1 to about 4 carbon atoms, which esters may be subsequently converted to diketones which are useful as metal extractants.

The acids which may be esterified may be defined by the formula:

RCOOH where R is an aliphatic or aromatic hydrocarbon radical, having up to about 21 carbon atoms. The acids may be the naturally occurring fatty acids having from about 6 to about 22 carbon atoms or may be synthetic acids such as those produced by the oxo process, which may have an odd number of carbon atoms.

The alcohols are preferably the lower alkyl alcohols and may ideally be represented by formula:

R'OH where R' is an aliphatic hydrocarbon radical having from 1 to about 4 carbon atoms. The alkanols such as methanol, ethanol and propanol are preferred, with methanol being the most preferred.

In the improved process of esterification of the present invention, the alcohol is employed in an excess over that stoichiometrically required to react with the acid. Accordingly, the molar ratio of alcohol to carboxylic acid will be greater than 1:1, and amounts up to about 4:1 may be employed. More desirably, the amount of alcohol employed will lie in the range of about 1.2 to 3 moles of alcohol per mole of acid with about 1.5 to 2.0 moles of alcohol to mole of acid being most preferred.

The sulfuric acid is employed in an amount sufficient to both catalyze the reaction and to serve as a dehydrating agent or desiccant for the by-product water. Accordingly, the sulfuric acid should be employed in an amount greater than about 0.05 moles per mole of carboxylic acid to be esterified and preferably above 0.1 moles and of sulfuric acid per mole of carboxylic acid, which is sufficient to both catalyze the dehydrate the water. Most desirably, from about 0.1 to about 0.5 moles of sulfuric acid and most preferably about 0.2 moles will be employed per mol of carboxylic acid. The reaction is carried out at elevated temperatures, conveniently reflux conditions. With methanol as the alcohol and a carboxylic acid having from about 6 to about 22 carbon atoms a temperature will be on the order of about 70° to about 100° C. However, temperatures on the order at about 40° to about 120° C. and more preferably 60° to about 80° C. will be employed. The specific temperature employed will be determined however by the specific alcohol employed and specific carboxylic acid to be esterified. In the laboratory reflux periods of about 1 to 2 hours were sufficient to provide yields of methyl isooctanoate in the methanol esterification of isooctanoic acid employing about 1.5 to about 2 moles of methanol per mole of isooctanoic acid which provided the ester of greater than 99% purity. In contrast, in reactions not using an excess of sulfuric acid (only a catalytic amount) time periods of reflux of about 10 hours or more were required to provide about an 80% yield of ester of lower purity even with a seven molar excess of methanol. Again, the reaction period will depend on the specific alcohol employed and specific acid to be esterified. Generally reaction periods will not need to exceed about 4 hours and the reaction will be complete (about 90% yield) usually within 1 to about 3 hours employing the preferred levels of carboxylic acid, alcohol and sulfuric acid. After completion of the esterification the sulfuric acid layer is removed and any unesterified acid is removed as the sodium salt by an alkaline aqueous wash. The ester may be dried by azeotropic distillation with an aliphatic hydrocarbon solvent such as heptane. The unreacted carboxylic acid in the aqueous alkaline wash can be recovered by acidification with an acid, preferably spent sulfuric acid, from the esterification step.

Where the ester is to be converted to a diketone such as 1-phenylisodecane-1,3-dione for use as a metal extractant, the high purity ester is then condensed with acetophenone as noted in U.S. Pat. No. 4,175,012 mentioned earlier.

To further illustrate the various objects and advantages of the present invention, the following examples are provided in which all parts and percentages are by weight unless otherwise indicated. It is understood their purpose is entirely illustrative and in no way intended to limit the scope of the invention.

EXAMPLE 1

In this example there is described the esterification of isooctanoic acid a branched carboxylic acid, with methanol in accordance with the present invention (A) using an excess of sulfuric acid and for comparative purposes esterification (B) using an excess of methanol with only a catalytic amount of sulfuric acid.

A. Following the present invention, 2 moles of methanol per mole of isooctanoic acid was employed with sufficient sulfuric acid (0.2 moles per mole of isooctanoic acid) to function both as a catalyst and water desiccant. The reaction was complete after about 2 hours at reflux temperature (about 70° C.). The unesterified isooctanoic acid was removed by an aqueous alkaline wash (sodium carbonate in water —10%). The resulting methyl isooctanoate ester was then azeotropically distilled with heptane, providing a 95% yield of ester of 99% purity.

B. In contrast to A above, a catalyzed esterification of isooctanoic acid with methanol using only a catalytic amount of sulfuric acid (0.015 moles of sulfuric acid per mole of isooctanoic acid) was carried out. To provide a high yield an excess of methanol was employed (8 moles of methanol per mole of isooctanoic acid). The reactants were then heated under reflux (70° C.) for about 10 hours. The sulfuric acid was neutralized with solid sodium carbonate after which the methanol and by-product water were removed by azeotropic distillation. The unreacted isooctanoic acid was removed as the sodium salt in an aqueous alkaline wash after which the ester was dried by azeotropic distillation with heptane. The yield of ester by this process was about 75-80%.

EXAMPLE 2

In this example, a series of larger scale esterifications was conducted employing a mixture of 1,000 kg of isooctanoic acid, 560 L of methanol and 70 L of concentrated sulfuric acid which was refluxed for 2 hours at about 70° C. A sample was submitted to the laboratory for verification that the reaction was at the 90 to 95% degree of completion. The reaction mixture was cooled to 60° C. and allowed to stand unagitated for 10 minutes for phase separation, after which the lower phase which contained sulfuric acid, water and methanol was removed. Unreacted isooctanoic acid and any residual sulfuric acid were neutralized and removed with 375 L of 10% sodium carbonate solution. The product was washed with 300 L of water. This wash step was repeated if the pH of the first wash was greater than 8. Addition of toluene and drying of the ester by azeotropic distillation was only done with the first 3 batches of ester. The ester in succeeding batches was left undried and without the addition of any solvent. Typical cycle time was 8 to 10 hours.

The product was analyzed for its content of isooctanoate ester and isooctanoic acid. Typical analyses were: 0.3% isooctanoic acid, balance ester. The average yield was about 92%.

EXAMPLE 3

This example illustrates the use of the ester in the conversion to a diketone which is useful as a metal extractant as described in U.S. Pat. No. 4,175,012.

The following is illustrative of the preparation.

A dispersion of 16.9 G (0.4 mole) of 56% by weight sodium hydride in mineral oil is slurried with n-pentane under nitrogen, the supernatant liquid is removed by suction with a sintered glass tip tube. This process is repeated three times before 500 ml of dry tetrahydrofuran and 75.8 G (0.48 mole) of methyl isooctanoate are added. The resultant mixture is heated to reflux temperature with agitation. A total of 48 G (0.4 mole) of acetophenone is added to the above refluxing mixture over a 3 hour period of time. The system is maintained at reflux temperature for an additional one half hour after the acetophenone addition is completed. Approximately 20 ml of methanol is added to the above mixture at room temperature to destroy any unreacted sodium hydride. The reaction mixture is then poured into a vigorously stirred mixture of 75 ml of concentrated hydrochloric acid and 250 G of ice. When most of the ice has melted the solution is extracted twice with 242 ml of heptane per extraction. The combined heptane extracts are successively washed with water, 10% sodium carbonate solution and again with water. The heptane solution is dried with sodium sulfate, filtered, the volatiles removed at reduced pressure and the residue distilled to yield 1-phenylisodecane-1,3-dione.

I claim:

1. A process of preparing an ester of an alcohol and an organic carboxylic acid comprising reacting said alcohol and said carboxylic acid at elevated temperature in the presence of sulfuric acid in an amount effective to both (a) catalyze the reaction of said alcohol and said carboxylic acid and (b) to remove the water of reaction whereby an ester of said alcohol and said carboxylic acid is provided.

2. A process as defined in claim 1 wherein said sulfuric acid is present in an amount in excess of 0.05 moles of sulfuric acid per mole of carboxylic acid.

3. A process as defined in claim 2 wherein said sulfuric acid is present in an amount up to about 0.5 moles of sulfuric acid per mole of carboxylic acid.

4. A process as defined in claim 3, wherein said sulfuric acid is present in an amount of 0.2 moles of sulfuric acid per mole of carboxylic acid.

5. A process as defined in claim 1 wherein said alcohol is employed in a stoicheometric excess over said carboxylic acid.

6. A process as defined in claim 5 wherein said alcohol is employed in a molar ratio in excess of 1:1 up to about 4:1 of alcohol to carboxylic acid.

7. A process as defined in claim 6 wherein the molar ratio of alcohol to carboxylic acid is in the range of about 1.2:1 to about 3:1.

8. A process as defined in claim 1 wherein the reaction temperature is in the range of about 40° to about 120° C.

9. A process as defined in claim 1 wherein said alcohol is methanol, said carboxylic acid is isooctanoic acid and the reaction time is maintained for about 1 to about 4 hours.

10. A process as defined in claim 9 wherein the reaction time is about 1 to about 3 hours.

11. A process as defined in claim 1 whereby the ester of said alcohol and said carboxylic acid is provided in a yield of about 80% or more.

12. A process as defined in claim 11 wherein the ester of said alcohol and said carboxylic acid is provided in a yield greater than 90%.

13. A process as defined in claim 11 wherein the purity of ester of said alcohol and said acid is greater than about 90%.

14. A process as defined in claim 13 wherein the purity of the ester of said alcohol and said carboxylic acid is about 99%.

15. A process as defined in claim 1 wherein said carboxylic acid has the formula

R COOH where R is an aliphatic or aromatic hydrocarbon radical having up to about 21 carbon atoms.

16. A process as defined in claim 1 wherein said alcohol has the formula

R' OH where R' is an aliphatic hydrocarbon radical having from 1 to about 4 carbon atoms.

17. A process as defined in claim 16 wherein the organic carboxylic acid contains from about 6 to about 22 carbon atoms.

18. A process as defined in claim 17 wherein said carboxylic acid is a branched chain carboxylic acid.

19. A process as defined in claim 17 wherein said alcohol is methanol.

20. A process as defined in claim 17 wherein said carboxylic acid is isooctanoic acid.

21. A process of preparing an ester of an alcohol and an organic carboxylic acid wherein said carboxylic acid has the formula RCOOH where R is aliphatic or aromatic hydrocarbon radical having from about 6 to about 21 carbon atoms, and said alcohol has the formula R'OH where R' is an aliphatic hydrocarbon radical having from 1 to about 4 carbon atoms, comprising (1) reacting said alcohol and said carboxylic acid at a temperature in excess of about 60° degrees Centigrade, and a time of from 1 to about 4 hours; in the presence of sulfuric acid in an amount in excess of about 0.05 moles of sulfuric acid per mole of carboxylic acid, effective to both (a) catalyze the reaction of said alcohol and said carboxylic acid and (b) unite with the water of reaction to immobilize the water of reaction; and an amount of alcohol in a molar ratio of alcohol to carboxylic acid in excess of 1:1 to about 4:1; whereby an ester of said alcohol and said carboxylic acid is provided in a yield of 80% or more and an ester purity greater than about 90%; and (2) recovering the ester.

22. A process as defined in claim 21 wherein said alcohol is methanol and said carboxylic acid is isooctanoic acid, the sulfuric acid is present in an amount of about 0.2 moles of sulfuric acid per mole of isooctanoic acid and said ester is provided in a yield greater than 90% and an ester purity of about 99%.

* * * * *